United States Patent
Seo et al.

(10) Patent No.: US 10,470,983 B2
(45) Date of Patent: *Nov. 12, 2019

(54) COSMETIC PACK AND MANUFACTURING METHOD THEREFOR

(71) Applicant: AMOLIFESCIENCE CO., LTD., Seoul (KR)

(72) Inventors: In Yong Seo, Seoul (KR); Ji Hyun Lee, Incheon (KR)

(73) Assignee: AMOLIFESCIENCE CO., LTD., Seoul (KR)

(*) Notice: Subject to any disclaimer, the term of this patent is extended or adjusted under 35 U.S.C. 154(b) by 5 days.

This patent is subject to a terminal disclaimer.

(21) Appl. No.: 15/902,347

(22) Filed: Feb. 22, 2018

(65) Prior Publication Data

US 2018/0177687 A1 Jun. 28, 2018

Related U.S. Application Data

(63) Continuation-in-part of application No. PCT/KR2016/009078, filed on Aug. 18, 2016.

(30) Foreign Application Priority Data

Aug. 24, 2015 (KR) .................. 10-2015-0118866

(51) Int. Cl.
| | |
|---|---|
| *A61K 8/02* | (2006.01) |
| *B32B 7/06* | (2019.01) |
| *B32B 27/12* | (2006.01) |
| *A45D 44/00* | (2006.01) |

(52) U.S. Cl.
CPC .......... *A61K 8/0212* (2013.01); *A45D 44/002* (2013.01); *B32B 7/06* (2013.01); *B32B 27/12* (2013.01)

(58) Field of Classification Search
CPC ........ A61Q 19/00; A61Q 13/00; A61Q 15/00; A61Q 17/04; A61Q 19/02; A61Q 19/06; A61Q 19/08; A61Q 19/10; A61K 8/0208; A61K 8/0212; A61K 8/731; A61K 8/86; A61K 8/0204; A61K 8/0216; A61K 8/027; A61K 8/345; A61K 8/65; A61K 8/678; A61K 8/735; A61K 8/8129; A61K 8/8176; A61K 8/8182; A61K 8/85; A61K 8/922

See application file for complete search history.

(56) References Cited

U.S. PATENT DOCUMENTS

| | | | | |
|---|---|---|---|---|
| 2006/0264140 | A1* | 11/2006 | Andrady | D01D 5/0061 442/341 |
| 2008/0069845 | A1* | 3/2008 | Makihara | A45D 44/002 424/401 |
| 2010/0069864 | A1* | 3/2010 | Berland | A61F 13/51305 604/370 |
| 2015/0125499 | A1* | 5/2015 | Ochiai | A45D 44/002 424/401 |
| 2015/0272855 | A1* | 10/2015 | Kim | A45D 34/04 424/401 |

FOREIGN PATENT DOCUMENTS

| | | | | |
|---|---|---|---|---|
| KR | 20110080066 | | 7/2011 | |
| KR | 2020130005141 | | 8/2013 | |
| KR | 10-2014-0052639 | * | 5/2014 | ............ A45D 44/22 |
| KR | 20140052639 | | 5/2014 | |
| KR | 1020140091449 | | 7/2014 | |
| KR | 1020150005074 | | 1/2015 | |
| KR | 10-2015-0030699 | * | 3/2015 | ............ A45D 44/00 |
| KR | 20150030699 | | 3/2015 | |

OTHER PUBLICATIONS

International Search Report—PCT/KR2016/009078 dated Nov. 23, 2016.

* cited by examiner

*Primary Examiner* — Audrea B Coniglio
(74) *Attorney, Agent, or Firm* — Cantor Colburn LLP (57) ABSTRACT

Provided is a beauty care pack including: a support; a shape retaining layer that is laminated on the support so as to be separated from the support by moisture and is formed by electrospinning a polymer material, to maintain moisturizing and hold the shape of the beauty care pack; and a chemical liquid layer that is laminated on the shape retaining layer and is formed by electrospinning a water-soluble polymer material and a functional material, and that is a dry type and melted by moisture, to thus be easily and conveniently stored and packaged, and conveniently used since the dry sheet is attached on the face of a user.

8 Claims, 5 Drawing Sheets

COSMETIC PACK AND MANUFACTURING METHOD THEREFOR

TECHNICAL FIELD

The present invention relates to a dry type beauty care pack (or a dry type cosmetic pack) in which a functional material is absorbed into a skin after being attached to the skin, and a method of manufacturing the beauty care pack.

BACKGROUND ART

Conventional general beauty care packs have been manufactured to contain essence including nutrients such as natural extracts, proteins, and vitamins on a woven fabric or a nonwoven fabric so as to have functions such as whitening, wrinkle reduction, moisture supply, relief from skin troubles, and allowance of skin elasticity.

However, since the conventional beauty care packs are manufactured on the basis of a woven fabric or a nonwoven fabric, sufficient adhesion is not achieved at the interface which is in contact with the skin, and thus effective ingredients cannot be sufficiently transferred to the deep part of the skin. In addition, an excessive amount of essence has been added to improve adhesive strength or power with respect to the skin.

Therefore, when a user makes an action actively with a conventional beauty care pack attached to the skin, the beauty care pack may fall or flow down due to the self-weight of the beauty care pack itself and the excessive essence may flow out, to thus result in uncomfortable and unpleasant feeling and also cause a loss of the essence. In addition, wearing a beauty care pack may often make it difficult for a wearer to take daily activities, and thus the wearer may have to lie down during the time of wearing the beauty care pack.

In order to overcome such disadvantages, hydrogel beauty care packs have recently been widely used. Since the hydrogel beauty care pack is excellent in the feeling of fit, a wearer who wears the hydrogel beauty care pack may perform daily activities, but the hydrogel beauty care pack is so thick to cause limited adhesion and to result in inconveniences of having to remove the hydrogel beauty care pack separately due to the flowing-down of the excessive essence or after the lapse of the wearing time.

Recently, nanofibers having a diameter of less than 1 μm have been actively studied using an electrospinning technique. These nanofibers are formed in a laminated structure having a three-dimensional pore structure at the same time of manufacture, and can provide a much larger skin contact area than conventional woven or nonwoven fabrics when used in the field of cosmetics. In addition, when manufacturing nanofibers, various functional materials are mixed with a spinning solution, and the spinning solution mixed with the various functional materials is spun, to then be manufactured in the form of nanofibers mounted with the functional materials.

As disclosed in Korean Patent Application Publication No. 10-2011-080066, a conventional mask pack has been proposed as a skin care pack, in which a double-layered nanofiber layer is formed on a nonwoven fabric, and the double-layered nanofiber layer is surface-treated with plasma. However, this technology includes the process of complexing the nanofiber layer on the nonwoven fabric and the secondary process such as the plasma treatment, to thereby increase the process cost.

In addition, a process such as lamination, thermal fusion, or ultrasonic bonding using a chemical adhesive or the like is required to make a composite of the nonwoven fabric and the nanofiber layer. When the adhesive or the like is not used, peeling between the nonwoven fabric and the nanofiber layer may happen due to the functional essence or moisture.

Furthermore, the nanofibers of the double-layered structure are spun in the form of a core/shell, in which the core portion is made of polyurethane or the like, and the shell portion contacting the skin is made of biodegradable polymers to minimize the trouble with the skin. However, in the case that 100% of the residual solvent is not removed due to the use of the toxic solvent, there is a problem of secondary contamination by the residual solvent.

Particularly, since most of the biodegradable polymers used in the conventional art are required to be hydrophilized through a plasma treatment process due to the hydrophobic properties of the biodegradable polymers, there may have problems of causing an increase in the process cost as well as causing deterioration of the functional material.

DISCLOSURE

Technical Problem

Accordingly, it is an object of the present invention to provide a beauty care pack which is manufactured in the form of a dry sheet by using a nanofiber web containing a functional material, to thus be easily and conveniently stored and packaged, and which is conveniently used since the dry sheet is attached on the face of a user, and a method of manufacturing the same.

It is another object of the present invention to provide a beauty care pack which includes a shape retaining layer to maintain moisturizing and hold the shape of the beauty care pack, and which includes a printed layer formed on the shape retaining layer to make a design beautiful, and a manufacturing method thereof.

It is still another object of the present invention to provide a beauty care pack including a shape retaining layer which is transparent in a wet state and is changed to a white color in a dried state, to thereby enable a user to recognize the time for removing the beauty care pack to thus be conveniently used.

Technical Solution

In order to attain the above object, according to an aspect of the present invention, there is provided a beauty care pack comprising: a support; a shape retaining layer that is laminated on the support so as to be separated from the support by moisture and is formed by electrospinning a polymer material, to maintain moisturizing and hold the shape of the beauty care pack; and a chemical liquid layer that is laminated on the shape retaining layer and is formed by electrospinning a water-soluble polymer material and a functional material, and that is a dry type and melted by moisture.

Preferably but not necessarily, the support may be formed of any one of a nonwoven fabric, a mesh, silicon, PET (polyethylene terephthalate), PE (polyethylene), PP (polypropylene) and PU (polyurethane).

Preferably but not necessarily, a release film may be attached to the chemical liquid layer which protects the chemical liquid layer and is separated from the chemical liquid layer, at use.

Preferably but not necessarily, when the support and the shape retaining layer are pressed together, the fibers of the support and the fibers of the shape retaining layer are mutually intertwined and mutually laminated, and when water is added to the shape retaining layer and thus the chemical liquid layer melts, the support and the shape retaining layer may be separated from each other.

Preferably but not necessarily, the shape retaining layer may be formed in the form of a nanofiber web shape having fine pores by electrospinning an electrospinnable spinning solution in which a polymer material and a solvent are mixed at a predetermined ratio.

Preferably but not necessarily, the shape retaining layer may be transparent in a state containing a solvent, and may be changed to a color which can be visually confirmed when the solvent is dried.

Preferably but not necessarily, a printed layer for design may be formed on one surface of the shape retaining layer.

Preferably but not necessarily, the chemical liquid layer may be formed by electrospinning an electrospinnable spinning solution in which a water-soluble polymer material, a functional material, and a solvent are mixed at a predetermined ratio.

Preferably but not necessarily, the water-soluble polymer materials may include one selected from polymer materials comprising polyvinyl pyrrolidone (PVP), polyvinyl alcohol (PVA), polyethylene oxide (PEO), carboxyl methyl cellulose (CMC), starch, polyacrylic acid (PAA), and hyaluronic acid, or a mixture of two or more thereof.

According to another aspect of the present invention, there is provided a method of manufacturing a beauty care pack, the method comprising the steps of: forming a shape retaining layer in the form of a nanofiber web by electrospinning a first spinning solution mixed with a polymer material and a solvent; forming a chemical liquid layer in the form of a nanofiber web by electrospinning a second spinning solution mixed with a water-soluble polymer material, a functional material and a solvent; laminating and compressing the support on the shape retaining layer so as to intertwine the fibers of the support and the fibers of the shape retaining layer to then be mutually laminated; and cutting and shaping the laminated beauty care pack.

Advantageous Effects

As described above, the present invention provides a beauty care pack which is manufactured in the form of a dry sheet by using a nanofiber web containing a functional material, to thus be easily and conveniently stored and packaged, and which is conveniently used since the dry sheet is attached on the face of a user, and a method of manufacturing the same.

In addition, the present invention provides a beauty care pack which includes a shape retaining layer to maintain moisturizing and hold the shape of the beauty care pack, and which includes a printed layer formed on the shape retaining layer to make a design beautiful, and a manufacturing method thereof.

In addition, the present invention provides a beauty care pack including a shape retaining layer which is transparent in a wet state and is changed to a white color in a dried state, to thereby enable a user to recognize the time for removing the beauty care pack to thus be conveniently used.

BEST MODE

Hereinafter, embodiments of the present invention will be described in detail with reference to the accompanying drawings. The sizes and shapes of the components shown in the drawings may be exaggerated for clarity and convenience. In addition, terms defined in consideration of the configuration and operation of the present invention may vary depending on the intention or custom of the user, the operator, and the like. Definitions of these terms should be based on the content of this specification.

Figure 1:
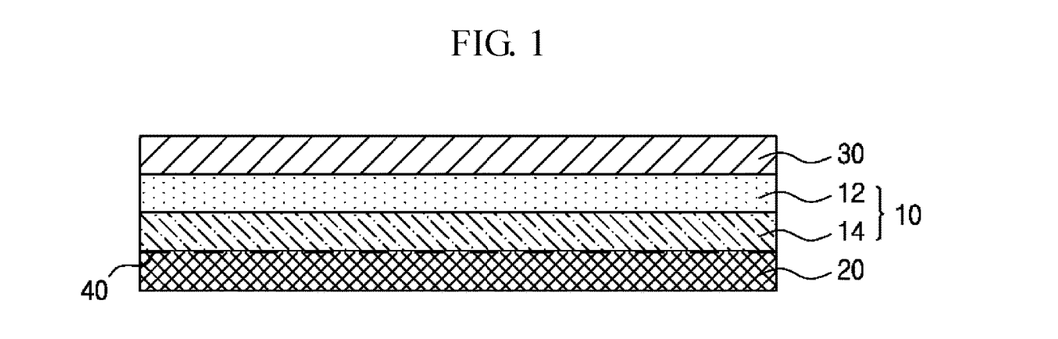
FIG. 1 is a cross-sectional view of a beauty care pack according to an embodiment of the present invention.

Referring to FIG. 1, a beauty care pack according to an embodiment of the present invention includes a support 20, a membrane 10 laminated on the support 20 and attached to a face, and a release film 30 which is laminated on the membrane 10 and separated from the membrane 10 when used.

The support 20 serves to support the membrane 10, and may be formed by using a nonwoven fabric. In addition to the nonwoven fabric, the support 20 may be made of various materials capable of supporting the beauty care pack such as silicon, PET (polyethylene terephthalate), PE (polyethylene), PP (polypropylene) and PU (polyurethane).

The support 20 may be formed by using a mesh capable of supporting the entire beauty sheet while making the design beautiful. The mesh is formed by weaving silver yarn, fiber yarn, aluminum wire, or resin yarn.

The release film 30 is made of PET, PP, PE material or release paper, and has strength enough to support the membrane 10.

The membrane 10 includes a shape retaining layer 14 that is laminated on the support 20 and is made of an electrospinnable polymer material, and a chemical liquid layer 12 that is laminated on the shape retaining layer 14 and is made of a water-soluble and electrospinnable polymer material and a functional material.

When the support 20 and the shape retaining layer 14 are pressed together, the fibers of the support 20 and the fibers of the shape retaining layer 14 are intertwined with each other, and laminated with each other, and when water is added to the shape retaining layer 14, the chemical liquid layer 12 is melted, the support 20 and the shape retaining layer 14 are separated from each other.

Therefore, when the membrane 10 is attached to the face and then water is added to the membrane 10, the support 20 can be easily separated from the membrane 10, and only the membrane 10, which is in a transparent state, is attached to the face, to thereby enable a user to feel convenient for activity after being attached to the face.

The shape retaining layer 14 is formed by mixing a water-soluble polymer and a solvent at an appropriate ratio to prepare an electrospinnable spinning solution, then electrospinning the spinning solution to form nanofibers having a fiber diameter of less than 3 µm, and laminating the nanofibers so as to be formed into a nanofiber web shape having fine pores.

The shape retaining layer 14 functions to maintain the shape of the membrane 10 when the membrane 10 is attached to the skin, and the essence sprayed on the skin is absorbed in the fine pores to serve as a moisturizer.

Here, since the shape retaining layer 14 is formed into a nanofiber web shape in which a polymer material is electrospun to accumulate nanofibers, diffused reflection disappears when the essence is absorbed, that is, in the state of containing a solvent, and thus the shape retaining layer 14 looks transparent. Meanwhile, when the essence does not exist, that is, when the solvent is in a dry state, the shape retaining portion 14 appears to be a white color or another color other than the white color. Therefore, it is possible to visually confirm that the chemical liquid portion 12 is completely absorbed to the skin.

In other words, conventional beauty care packs should be separated from the face when a predetermined period of time has elapsed after being attached to the skin. However, the time taken for the beauty care pack to be absorbed by the skin is different depending on persons. Therefore, if the beauty care pack is removed at a predetermined time, the functional material contained in the beauty care pack may not be completely absorbed into the face, or the beauty care pack may remain attached to the face while the functional material is completely absorbed.

Since the shape retaining layer 14 of the present invention changes from transparent color to white color when the solvent is dried, the time for separating the beauty care pack from the face can be visually confirmed to thereby conveniently use the beauty care pack.

Here, any material can be used as the solvent as long as a material can be a safe material that can dissolve the water-soluble polymer constituting the chemical solution layer such as moisture, essence, and mist, and that does not cause skin troubles or the like.

The polymer material forming the shape retaining layer 14 may employ any electrospinnable polymer material, and also employ other polymer materials other than the water-soluble polymer material.

A printed layer 40 may be formed on one side of the shape retaining portion 14 to enhance the advertising patterns or design.

The chemical liquid portion 12 is formed by mixing a water-soluble polymer, a functional material and a solvent at an appropriate ratio to prepare a spinning solution, then electrospinning the spinning solution to form nanofibers having a fiber diameter of less than 3 µm, and laminating the nanofibers so as to be formed into a nanofiber web shape.

Since the chemical liquid layer 12 is a mixture of a water-soluble polymer material and a functional material, the functional material is absorbed by the skin when the chemical liquid layer 12 is adhered to the skin, and the water-soluble polymer material is absorbed by the support 20 to perform a moisturizing function.

By using water or alcohol as the solvent contained in the spinning solution for forming the chemical solution layer 12, it is possible to prevent skin troubles and the like caused by the use of conventional organic solvents.

The spinning method that may be applied for the present invention may employ any one of general electrospinning, air-electrospinning (AES), electrospray, electrobrown spinning, centrifugal electrospinning, and flash-electrospinning.

The water-soluble polymer material may employ synthetic polymers or natural polymers that may be electrospun. The synthetic polymers or natural polymers may be used alone or in combination thereof, but any polymers that may be dissolved in water or alcohol to form nanofibers by electrospinning are not particularly limited.

Examples of such water-soluble polymer materials may include one selected from polymer materials including polyvinyl pyrrolidone (PVP), polyvinyl alcohol (PVA), polyethylene oxide (PEO), carboxyl methyl cellulose (CMC), starch, polyacrylic acid (PAA), and hyaluronic acid, or a mixture of two or more thereof.

One of ingredients (such as albutine, niacinamide, and ascorbyl glucoside) that help skin whitening, ingredients (such as retinol and adenosine) that help to improve skin wrinkles, ingredients (such as titanium dioxide) that help to block ultraviolet rays, ingredients (such as snail mucus filtrate, acetyl hexapeptide, red ginseng collagen, aquaceramide, regenerating peptide, and galactomirase fermentation broth) that help moisturizing and skin elasticity, or a mixture of two or more thereof, may be used as the functional material.

In addition, the functional material may comprise one or a mixture of two or more selected from water-soluble collagen, vegetable platinum, tocopherol, xylitol and plant extract.

The crosslinking agent or co-crosslinking agent may be formed of one selected from para-toluene sulfonic acid (TSA), polyurea-co-formaldehyde, tri-methylpropane trimethacrylate (TMPTMA), divinylbenzene (DVB), N-(1-hydroxy-2,2-dimethoxyethyl) acrylamide, N,N'-methylenebisacrylamide, ethylene glycol diacrylate, di(ethylene glycol) diacrylate, boric acid, and glutaraldehyde, or a mixture of two or more thereof.

Figure 2:
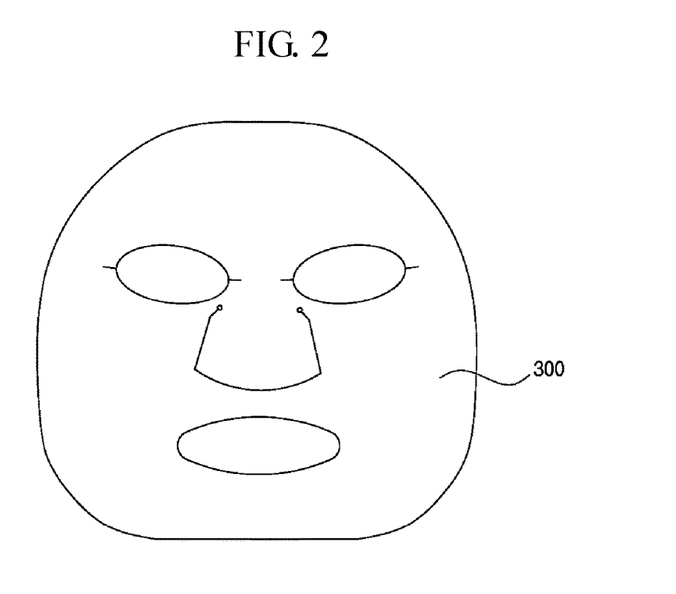
FIG. 2 is a plan view of a beauty care pack according to an embodiment of the present invention.
Figure 3:
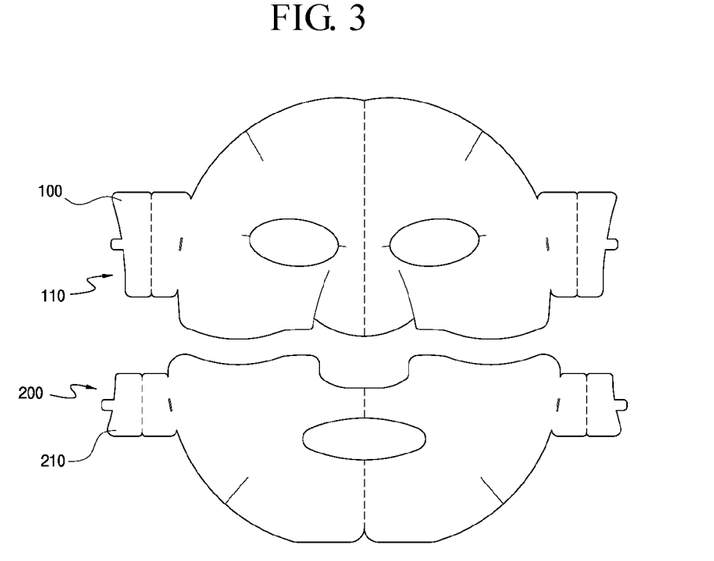
FIG. 3 is a plan view of a beauty care pack according to another embodiment of the present invention.

As shown in FIG. 2, the beauty care pack of the present invention may be formed into a shape of a sheet of a beauty care pack 300 enclosing an entire face, or as shown in FIG. 3, the beauty care pack of the present invention may be formed into a shape including a top beauty care pack 100 attached to an upper part of a face and a lower beauty pack 200 attached to a lower part of the face.

As shown in FIG. 3, since the separation knob or knobs 110 are formed in the beauty care pack, the release film 30 and the membrane 10 can be separated from each other, when holding and tearing off the separation knob or knobs 110. Accordingly, the separation operation of the release film 30 and the membrane 10 is easy and convenient, and the membrane 10 can be prevented from being damaged or contaminated.

The beauty care pack of the present invention can be applied to a type of attaching to other parts such as a neck or a hand of a body in addition to a mask pack attached to the face.

The manufacturing process of the beauty care pack will be described below.

Figure 4:
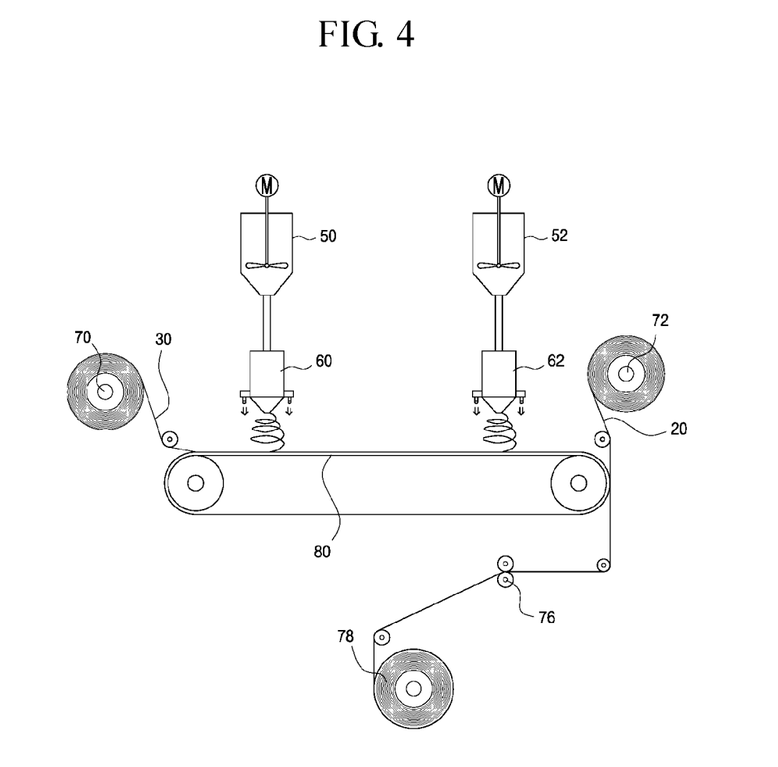
FIG. 4 is a configuration diagram of a beauty care pack manufacturing apparatus according to an embodiment of the present invention.

FIG. 4 is a configuration diagram of a beauty care pack manufacturing apparatus according to an embodiment of the present invention.

The beauty care pack manufacturing apparatus of the present invention comprises a first storage tank 50 in which a first spinning solution mixed with a polymer material and a solvent is stored, a second storage tank 52 in which a second spinning solution mixed with a water-soluble polymer material, a functional material and a solvent is stored, a first spinning nozzle 60 connected to a high voltage generator and connected to the first storage tank 50 to form a chemical solution layer 12; and a second spinning nozzle 62 connected to the high voltage generator and connected to the second storage tank 52 to form a shape retaining layer 14.

A collector 80 is provided below the first spinning nozzle 60 and the second spinning nozzle 62 to sequentially stack the chemical solution layer 12 and the shape retaining layer 14. By applying a high voltage electrostatic force of 90 to 120 Kv between the collector 80 and the first spinning nozzle 60 and between the collector 80 and the second spinning nozzle 62, the nanofibers are emitted and the nanofibers are accumulated in the collector 80 to form a nanofiber web.

A release film roll 70 wound with the release film 30 is provided in front of the collector 80 and a support roll 72 wound with the support 20 is provided at the rear of the collector 80.

Figure 5:
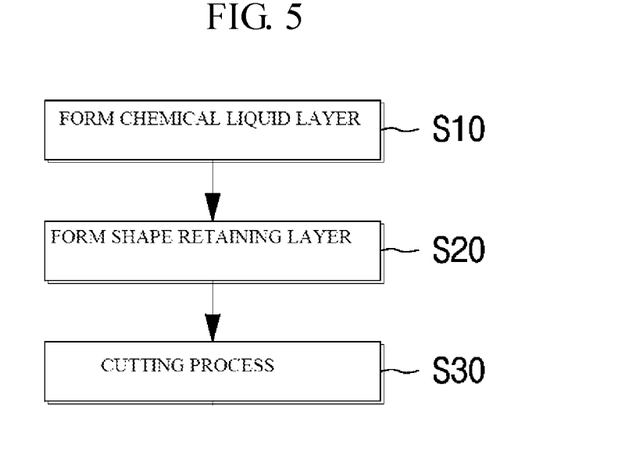
FIG. 5 is a flowchart showing a method of manufacturing a beauty care pack according to a first embodiment of the present invention.

The beauty care pack manufacturing method according to the first embodiment will be described below with reference to FIG. 5.

First, when the collector 80 is driven, the release film 30 wound around the release film roll 70 is supplied to the upper surface of the collector 80.

By applying a high voltage electrostatic force between the collector 80 and the first spinning nozzle 60, the first spinning nozzle 60 emits the first spinning solution to the release film 30 in the form of nanofibers. Then, the nanofibers are accumulated on the release film 30 to form a chemical liquid layer in the form of a nanofiber web (S10).

When the chemical liquid layer 12 is completed, the collector 80 is driven so that the chemical liquid layer 12 is moved to the lower portion of the second spinning nozzle 62 and the second spinning nozzle 62 electrospins the second spinning solution by applying a high voltage electrostatic force between the collector 80 and the second spinning nozzle 62. Then, the second spinning solution is spun to the chemical liquid layer 12, and nanofibers are accumulated in the chemical liquid layer 12 to form the shape retaining layer 14 having fine pores (S20).

Here, the content of the functional material contained in the third spinning solution may be set in the range of 10 to 50 wt %, relative to the water-soluble polymer, so that the beauty care effect can be exerted.

Then, the support 20 wound around the support roll 72 and the shape retaining layer 14 are laminated with each other. Here, when the support 20 and the shape retaining layer 14 are pressed together, the fibers of the support 20 and the fibers of the shape retaining layer 14 are intertwined with each other and laminated with each other. The support 20 and the shape retaining layer 14 that have been laminated with each other are separated from each other when water is introduced into the membrane 10 and thus the chemical liquid layer 12 is melted.

A printed layer 40 may be formed on one surface of the shape retaining layer 14 to enhance the design or provide advertising patterns.

As described above, the beauty care pack, which has completed the manufacturing process, is formed in the form of being attached to a face or a body part by performing a cutting process (S30).

Figure 6:
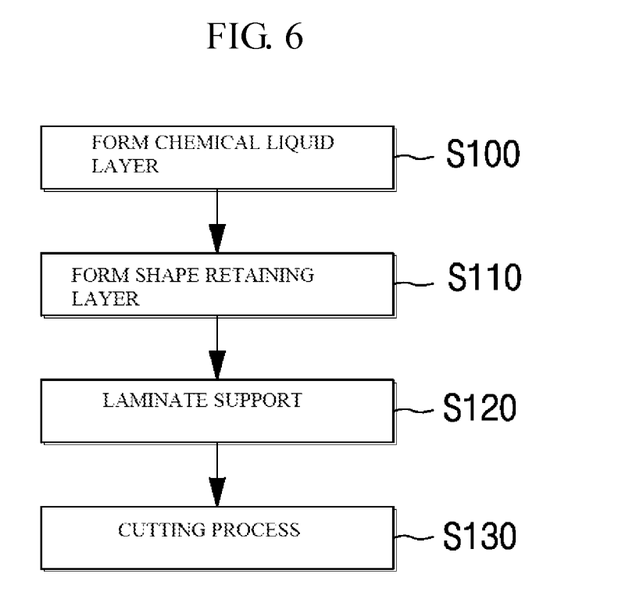
FIG. 6 is a flowchart showing a method of manufacturing a beauty care pack according to a second embodiment of the present invention.

The beauty care pack manufacturing method according to the second embodiment will be described below with reference to FIG. 6.

First, a chemical solution layer 12 is formed (S100). When a spinning solution containing a mixture of a water-soluble polymer, a functional material and a solvent is spun out from a spinning nozzle, nanofibers are produced and are accumulated to form a nanofiber web-like chemical liquid layer 12.

Then, the shape retaining layer 14 is formed separately from the chemical liquid layer 12 (S110). An electrospinnable spinning solution mixed with a polymer material and a solvent is spun from a spinning nozzle to produce nanofibers and the nanofibers are accumulated to form the shape retaining layer 14 having fine pores.

A printed layer 40 may be formed on one side of the shape retaining layer 14 to enhance the design.

Then, the chemical solution layer 12 and the shape-retaining layer 14 are laminated on the support 20 (S120). That is, after the chemical liquid layer 12 and the shape retaining layer 14 are separately prepared, the shape retaining layer 14 and the chemical liquid layer 12 are successively laminated on the support 20.

Then, the completely manufactured beauty care pack is cut to form a face shape or a shape that can be attached to a specific part of the body (S130).

Figure 7:
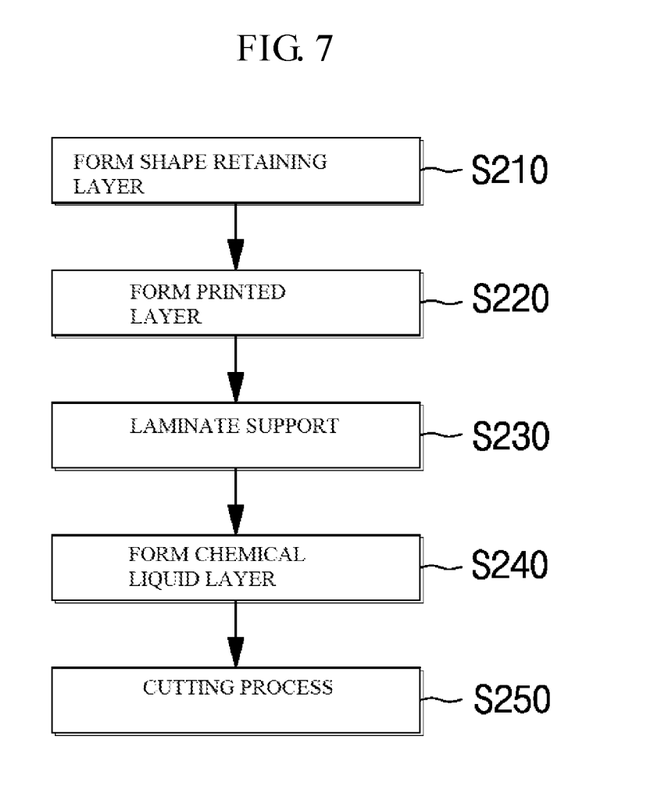
FIG. 7 is a flowchart showing a method of manufacturing a beauty care pack according to a third embodiment of the present invention.

The beauty care pack manufacturing method according to the third embodiment will be described below with reference to FIG. 7.

First, a shape retaining layer 14 is formed (S210). An electrospinnable spinning solution mixed with a polymer material and a solvent is spun from a spinning nozzle to produce nanofibers and then the nanofibers are accumulated to form the shape retaining layer 14 having fine pores.

A printed layer 40 may be formed on one side of the shape retaining layer 14 to enhance the design (S220).

Then, the shape retaining layer 14 is laminated on the support 20 (S230). In this case, one surface of the shape retaining layer 14 on which the printed layer 40 is formed is attached to the support 20.

Then, the chemical liquid layer 12 is formed (S230). Here, the chemical liquid layer 12 may be separately formed from the shape retaining layer 14 and may be laminated on the other surface of the shape retaining layer 14, and may be electrospun directly on the other surface of the shape retaining layer 14, to thus form the chemical liquid layer 12.

Then, the completely manufactured beauty care pack is cut to form a face shape or a shape that can be attached to a specific part of the body (S250).

While the present invention has been particularly shown and described with reference to exemplary embodiments thereof, by way of illustration and example only, it is clearly understood that the present invention is not to be construed as limiting the present invention, and various changes and modifications may be made by those skilled in the art within the protective scope of the invention without departing off the spirit of the present invention.

INDUSTRIAL APPLICABILITY

The beauty care pack according to an embodiment of the present invention is formed as a dry type, and when moisture is added to the face after being attached to the face, the functional material is melted and absorbed by the skin, to thereby enable an easy and convenient storage and package, and enable an open field activity after being attached to the face.

What is claimed is:
1. A beauty care pack comprising:
   a dried shape retaining layer, the dried shape retaining layer being formed of a first nanofiber web having pores, wherein the first nanofiber web is formed of accumulated first nanofibers, and the first nanofibers are formed of a water-insoluble polymer;

a dried chemical layer laminated directly on one surface of the dried shape retaining layer, the dried chemical layer being formed of a second nanofiber web, wherein the second nanofiber web is formed of accumulated second nanofibers, and the second nanofibers are formed of a water-soluble polymer and a functional material; and a porous support detachably attached to the other surface of the dried shape retaining layer, wherein, when a moisture is applied to the porous support, the moisture is permeated into the dried chemical layer through the pores of the dried shape retaining layer, wherein the water-soluble polymer of the dried chemical layer is solved by the moisture and absorbed into the pores of the dried shape retaining layer along with the functional material, thereby the functional material becomes wet inside the pores of the dried shape retaining layer, thereby being effective on a user's skin.

2. The beauty care pack of claim 1, wherein the porous support is formed of any one of a nonwoven fabric, a mesh, silicon, PET (polyethylene terephthalate), PE (polyethylene), PP (polypropylene) and PU (polyurethane).

3. The beauty care pack of claim 1, wherein a release film is attached to the dried chemical layer which protects the dried chemical layer and is separated from the dried chemical layer before using the beauty care pack.

4. The beauty care pack of claim 1, wherein the dried shape retaining layer is configured to have a color when the moisture is dried.

5. The beauty care pack of claim 1, wherein a printed layer is formed on the other surface of the dried shape retaining layer.

6. The beauty care pack of claim 1, wherein the accumulated second nanofibers include: electrospun and accumulated nanofibers.

7. The beauty care pack of claim 1, wherein the water-soluble polymer includes one selected from polyvinyl pyrrolidone (PVP), polyvinyl alcohol (PVA), polyethylene oxide (PEO), carboxyl methyl cellulose (CMC), starch, polyacrylic acid (PAA), hyaluronic acid, and a mixture of two or more thereof.

8. The beauty care pack of claim 1, wherein the functional material is in a range of 10 to 50 wt % with respect to the water-soluble polymer.

* * * * *